(12) United States Patent
Brown (10) Patent No.: US 10,258,345 B2
(45) Date of Patent: Apr. 16, 2019

(54) SURGICAL LIGATION CLIP

(71) Applicant: Geoff Brown, Cottonwood Height, UT (US)

(72) Inventor: Geoff Brown, Cottonwood Height, UT (US)

( * ) Notice: Subject to any disclaimer, the term of this patent is extended or adjusted under 35 U.S.C. 154(b) by 210 days.

(21) Appl. No.: 15/164,764

(22) Filed: May 25, 2016

(65) Prior Publication Data

US 2017/0209151 A1    Jul. 27, 2017

(51) Int. Cl.
*A61B 17/122* (2006.01)

(52) U.S. Cl.
CPC ................... *A61B 17/122* (2013.01)

(58) Field of Classification Search
CPC ...... A61B 2017/1225; A61B 17/12031; A61B 17/1227; A61B 17/122; A61B 17/12022; A61B 17/12109
See application file for complete search history.

(56) References Cited

U.S. PATENT DOCUMENTS

| 5,938,666 | A | * | 8/1999 | Reynolds | ............. | A61B 17/122 |
| | | | | | | 606/120 |
| 2009/0171380 | A1 | * | 7/2009 | Whiting | ............... | A61B 17/122 |
| | | | | | | 606/158 |
| 2014/0243862 | A1 | * | 8/2014 | Bagaoisan | ........... | A61B 17/122 |
| | | | | | | 606/157 |

* cited by examiner

*Primary Examiner* — Eric J Rosen
*Assistant Examiner* — Chima U Igboko
(74) *Attorney, Agent, or Firm* — Steven Rinehart (57) ABSTRACT

A polymeric, surgical clip is provided for clamping a blood vessel between two legs. A hook section of the clip comprises, in some embodiments, a sharpened forward edge and/or a sharpened rearward edge for penetrating connective tissue adjacent a vessel before closing the surgical about a blood vessel. The upper leg of the surgical clip may comprise an oblique flank for disposing over the one or more edge of the hook section, preventing damage to soft connective tissue surrounding the surgical clip postoperatively.

11 Claims, 7 Drawing Sheets

SURGICAL LIGATION CLIP

FIELD OF THE INVENTION

This invention relates to surgical clips used to stop blood flow through blood vessels during surgery, and more particularly relates to a ligation clip for piercing connective tissue and locking down on a blood vessel.

BACKGROUND

Description of the Related Art

Typically, during open surgery, blood vessels, including veins or arteries, must be ligated to stop blood flow to a surgical site. In some cases, physicians must cut these vessels, or in other cases restrict them. Ligation is realized using a ligation clips which are relatively easy and quick to apply. Accordingly, the use of ligating clips in endoscopic as well as open surgical procedures has grown dramatically.

The ligation clips are applied to the blood vessel using a hemostatic ligation clip applier. Blood vessels remain ligated after surgery until occlusion occurs. Although in the past, surgical or ligation clips have been fabricated from metal, most current ligation clips are polymeric to prevent interference from the clip with imaging devices, including x-ray and MRI machines.

Typical ligation clips in the art are blunt and/or do not pierce soft connective tissue surrounding a blood vessel in surgically efficient manner. It also cumbersome to remove ligation clips from blood vessels, sometimes resulting in ligation clips being mistakenly left in the soft tissue or patients, or collateral soft tissue being damaged with removal.

A clip applier specifically designed for asymmetric plastic clips is used to close the clip around the tissue to be ligated, and to latch or lock the clip in the closed condition. When compressed the clip applier forces the legs of traditional clips inward and locks them together around a blood vessel.

Although polymeric ligation clips are in the art, current clips suffer from several inefficiencies, including that current clips do not efficiently pierce soft tissue and leave sharpened edges exposed to cut, damage and irritate tissue during surgery. A device which overcomes these inefficiencies is desirable.

SUMMARY

From the foregoing discussion, it should be apparent that a need exists for an improved surgical ligation clip. Beneficially, such a device would overcome inefficiencies with the prior art by providing a clip which could more efficiently penetrate soft tissue and prevent soft tissue damage.

The present invention has been developed in response to the present state of the art, and in particular, in response to the problems and needs in the art that have not yet been fully solved by currently available systems and apparati. Accordingly, the present invention has been developed to provide a polymeric surgical ligation clip, the surgical clip comprising: a concave lower leg having a proximal end and a distal end; a concave upper leg having a proximal end hingedly connected to the proximal end of the lower leg; a plurality of teeth protruding outwardly from one or more of the lower leg and the upper leg; a hook section jutting outwardly from the lower leg, the hook section defining a latching recess for engaging a distal end of the upper leg, hook section having a leading edge, the leading edge sharpened for incising soft tissue when the surgical clip is inserted into soft tissue; an oblique flank connected to the distal end of the upper leg, the oblique flank protruding outwardly from the upper leg, the oblique flank configured to dispose over the leading edge to prevent damage to soft tissue during surgery.

The lower edge of the oblique flank may define a groove for receiving the leading edge of the hook section when the surgical clip is closed. The distal end of the upper leg may further comprise a distal tooth for piercing soft tissue.

The surgical clip may further comprising a plurality of bosses for engaging jaws of an applier. A stress cavity may be formed at the connection point of the upper leg and the lower leg.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention may be practiced without one or more of the specific features or advantages of a particular embodiment. In other instances, additional features and advantages may be recognized in certain embodiments that may not be present in all embodiments of the invention.

These features and advantages of the present invention will become more fully apparent from the following description and appended claims, or may be learned by the practice of the invention as set forth hereinafter.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. In the following description, numerous specific details are provided to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

The schematic flow chart diagrams included herein are generally set forth as logical flow chart diagrams. As such, the depicted order and labeled steps are indicative of one embodiment of the presented method. The order in which a particular method occurs may or may not strictly adhere to the order of the corresponding steps shown.

Figure 1:
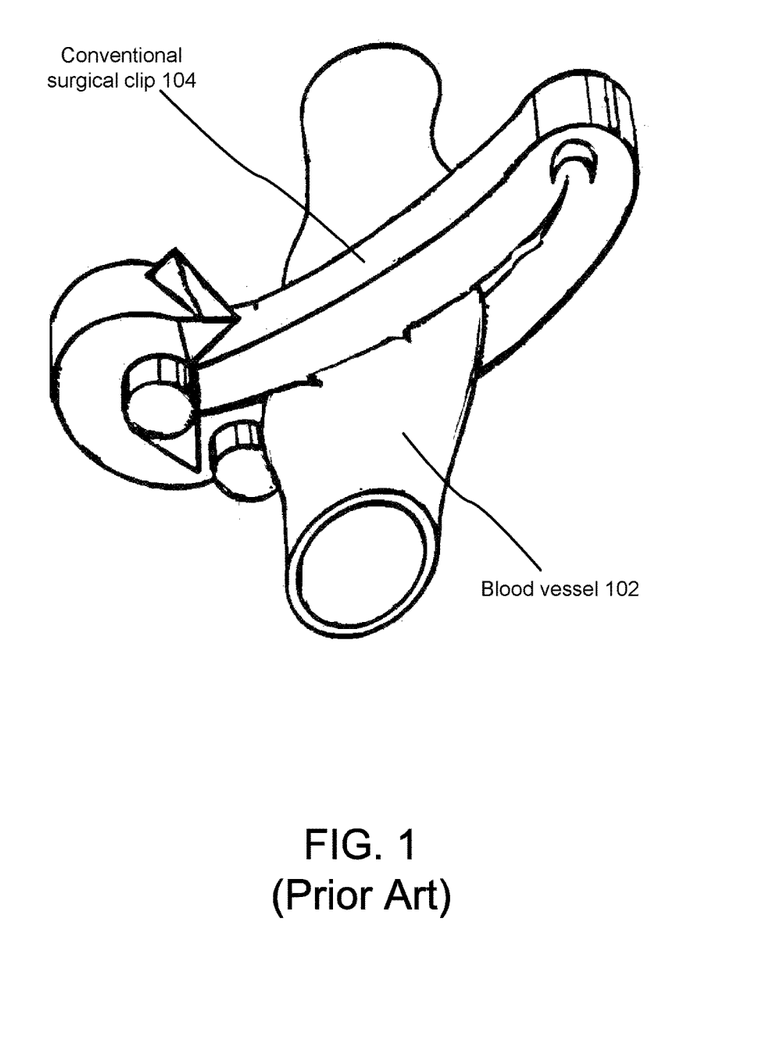
FIG. 1 is a traditional ligation clip in accordance with the prior art.

FIG. 1 is a traditional ligation clip in accordance with the prior art.

As shown, the conventional surgical clip 104 clamps down on a blood vessel 102. The surgical clip 104 is inserted using a specialized clamping or crimping tool (i.e. forceps). A hook portion of the surgical clip 104 clamps down on the blood vessel 102 and ligates the blood vessel 102.

The surgical clip 104 may be made of biodegradable materials and comprises latching means to keep the surgical clip 104 closed. Typically the surgical clip 104 is left in place permanently.

Figure 2:
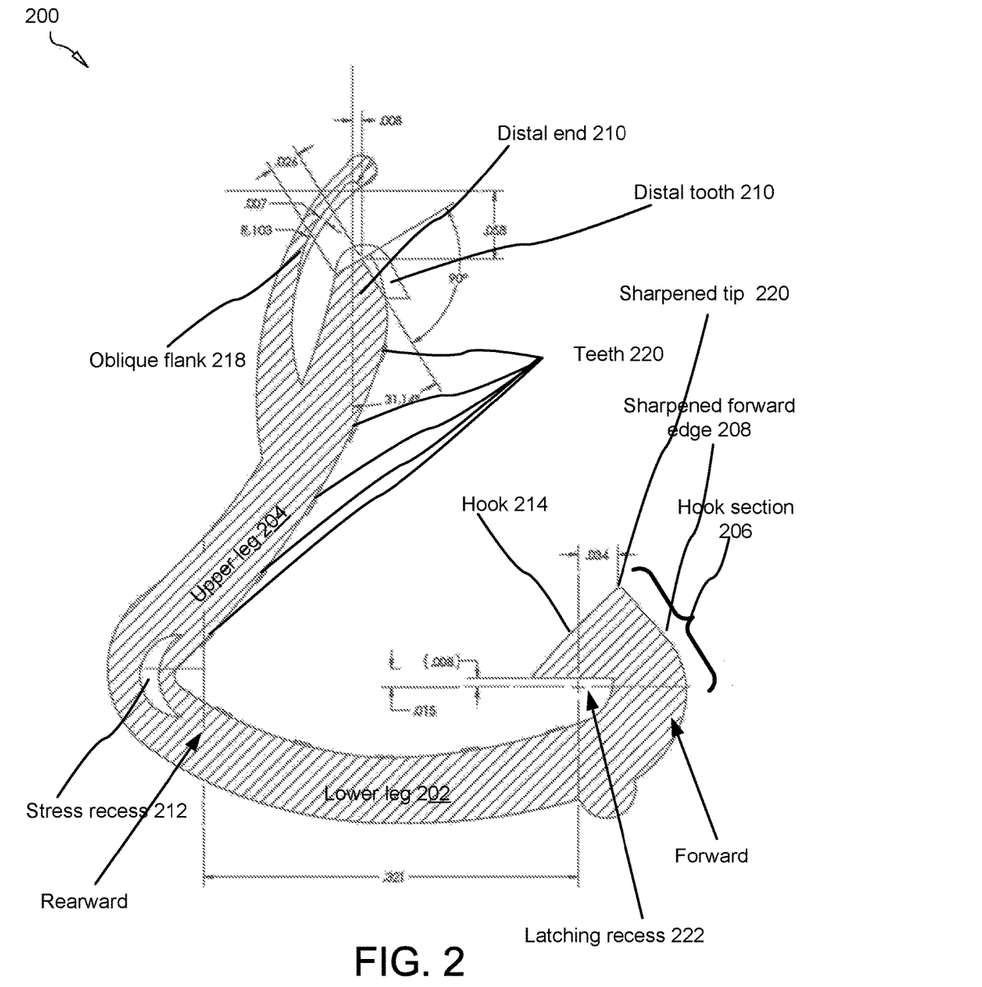
FIG. 2 is a side perspective view of an improved surgical ligation clip in accordance with the present invention.

FIG. 2 is a side perspective view of an improved surgical ligation clip 200 in accordance with the present invention. The surgical clip 200 comprises a lower leg 202; an upper leg 204; hook section 206 having a sharpened forward edge 208, a sharpened tip 220 and a hook 214; an oblique flank 218; a distal tooth 210; and a stress recess 212.

The surgical clip 200 may be fabricated from polymeric, metallic, and/or biodegradable materials. The use of polymeric and/or biodegradable materials to form the surgical clip 200 may beneficially render the surgical clip radio opaque for imaging purposes.

The lower leg 202 and upper leg 204 comprises elongated convex members hingedly connected at their rearward ends. The connection point between the legs 202, 204 defines a stress recess 212 for relieving tensile forces exerted across the hinge or connection point between the legs 202, 204 by a closing or closed clip 200 in the latched position (the clip 200 is shown in the open position).

The tip of the hook section 206 may be sharpened to pierce soft tissue when the clip 200 in closed within a patient during surgery. For this reason, the tip 220 of the hook section 206 of the clip 200 protrudes upwardly away from the lower leg in tooth-like fashion.

The inner surface of the leg 204 is contoured to match the outer (i.e., upper) surface of the leg 202 (both have approximately the same radius curvature) for extending compressive or tensile force uniformly across the legs 202, 204.

The clip 200 comprises a peninsular hook section 206, which protrudes, in the shown embodiment, in triangular fashion, from the lower leg 202 and which cantilevers back over the inner surface of the lower leg 202 forming a latching recess 222. The hook section 206 latches over the distal end 210 of the upper leg 204 when the clip 200 is compressed into closed.

In the closed position, the oblique flank 218 may be configured to clamp down over the sharpened forward edge 208 of the hook section 206 (or additionally or alternatively a corresponding sharpened rearward edge further described below), covering the sharpened forward edge 208 and preventing the edge 208 from incising, piercing, or agitating soft tissue in position operatively or post-operatively.

Figure 3:
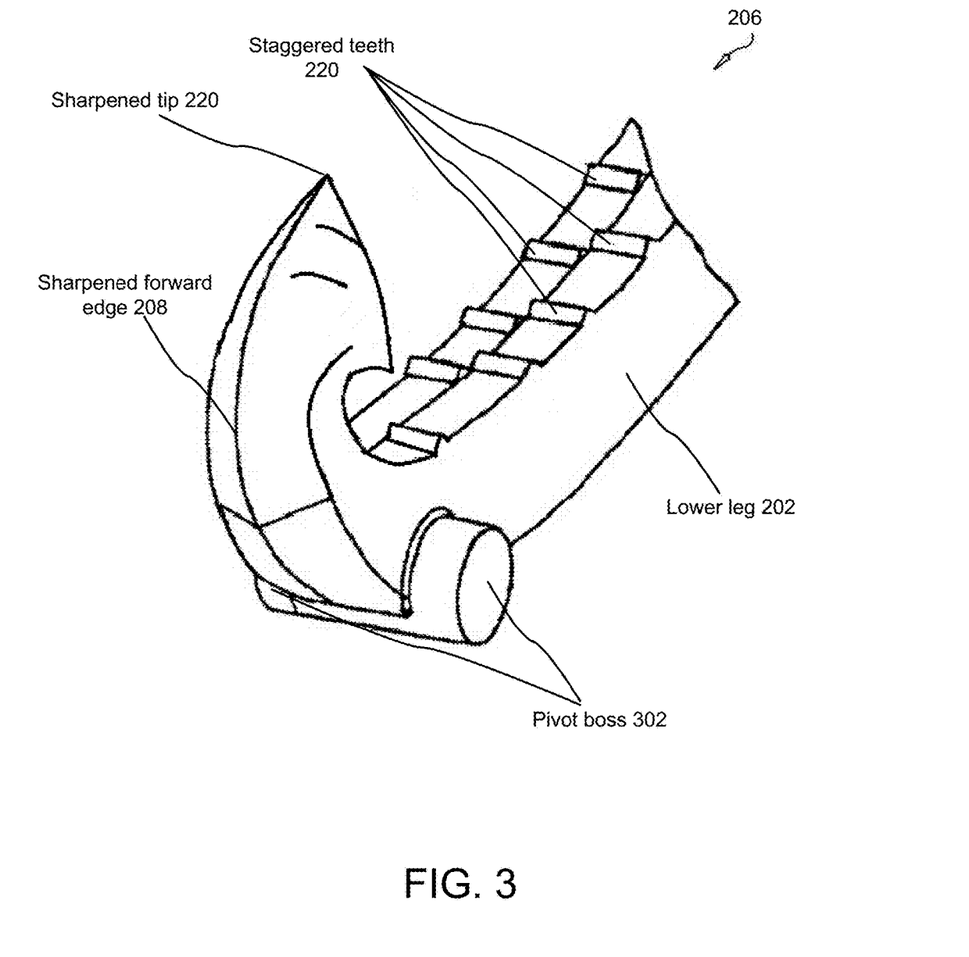
FIG. 3 is an upper-elevational side perspective view of the hook section of an improved surgical ligation clip in accordance with the present invention.

FIG. 3 is an upper-elevational side perspective view of the hook section 206 of an improved surgical ligation clip in accordance with the present invention.

As shown, the inner edge of the lower leg 202 comprises a plurality of staggered teeth 252. The teeth 252 in the shown embodiment are staggered along opposing sides of the inner edge of the lower leg 202. In some embodiments, the teeth 252 are not staggered on alternating sides of the inner edge of the lower leg 202, but rather span the entire width of the inner edge of the lower leg 202 are regular or irregularly-spaced intervals.

The forward edge 208 of the hook section 206 is sharpened in the shown embodiment to facilitate incising or piercing of soft tissue as the clip 200 in inserted into an anesthetized patient during surgery.

Figure 4:
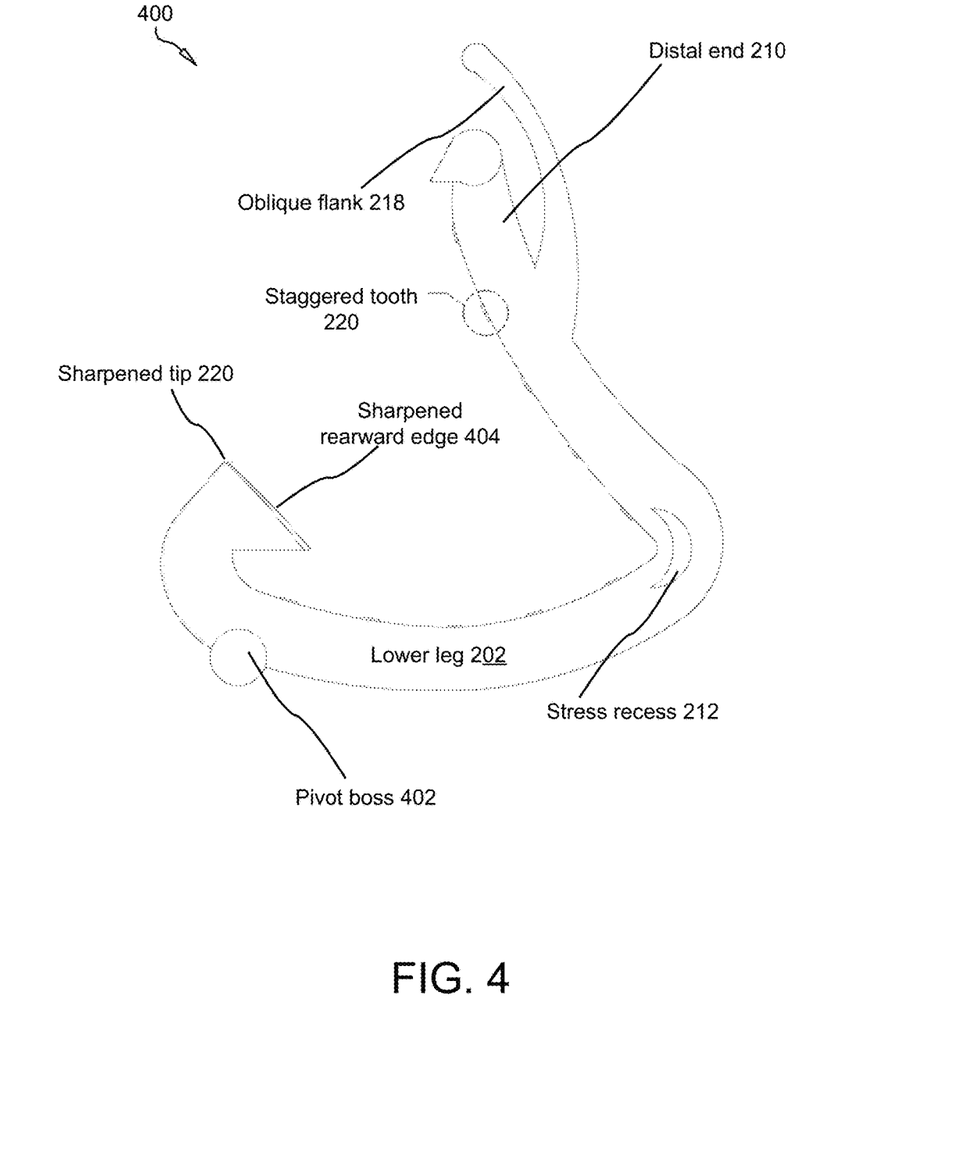
FIG. 4 is a side perspective view of an improved surgical ligation clip in accordance with the present invention.

FIG. 4 is a side perspective view of an improved surgical ligation clip 400 in accordance with the present invention. The clip 400 comprises a plurality of bosses 302.

The bosses 302 are cylindrical in the shown embodiments, and protrude laterally from the body lower leg 202. The bosses 302 allow an applicator, or clamping tool (i.e. forceps) to engage the clip 400 and insert the clip 400 in open or semi-open position into soft tissue during the operative phase of surgery by a surgeon, as known to those of skill in the art.

The clip 400 also comprises a sharpened rearward edge 404. Like the sharpened forward edge 208, the sharpened rearward edge 404 cuts soft tissue. As the clip 400 is closed, soft tissue disposed between the hook section 206 and the distal end 210 is incised; the clip 400 is closed; the distal end 210 is secured in latched position beneath the cantilevered hook section 206; and the oblique flank 218 orients over the sharpened rearward edge 404.

Figure 5:
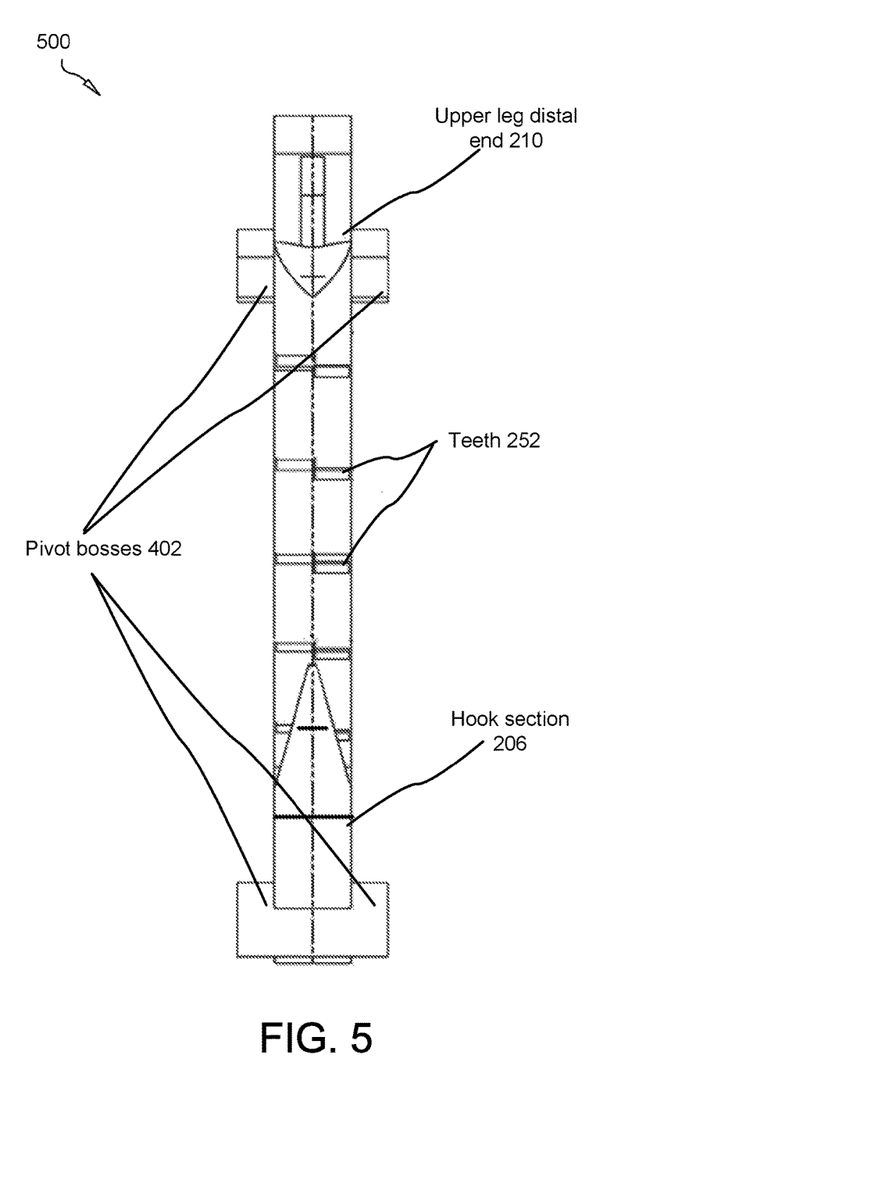
FIG. 5 is a top perspective view of an improved surgical ligation clip in accordance with the present invention.

FIG. 5 is a top perspective view of an improved surgical ligation clip 500 in accordance with the present invention. The staggered teeth 252 are disposed on the inner edge of the lower leg 202. The surgical clip 500 comprises four pivot bosses 402 (two on the lower leg 202 and two on the upper leg 204), but may comprise more-or-less than four.

Figure 6:
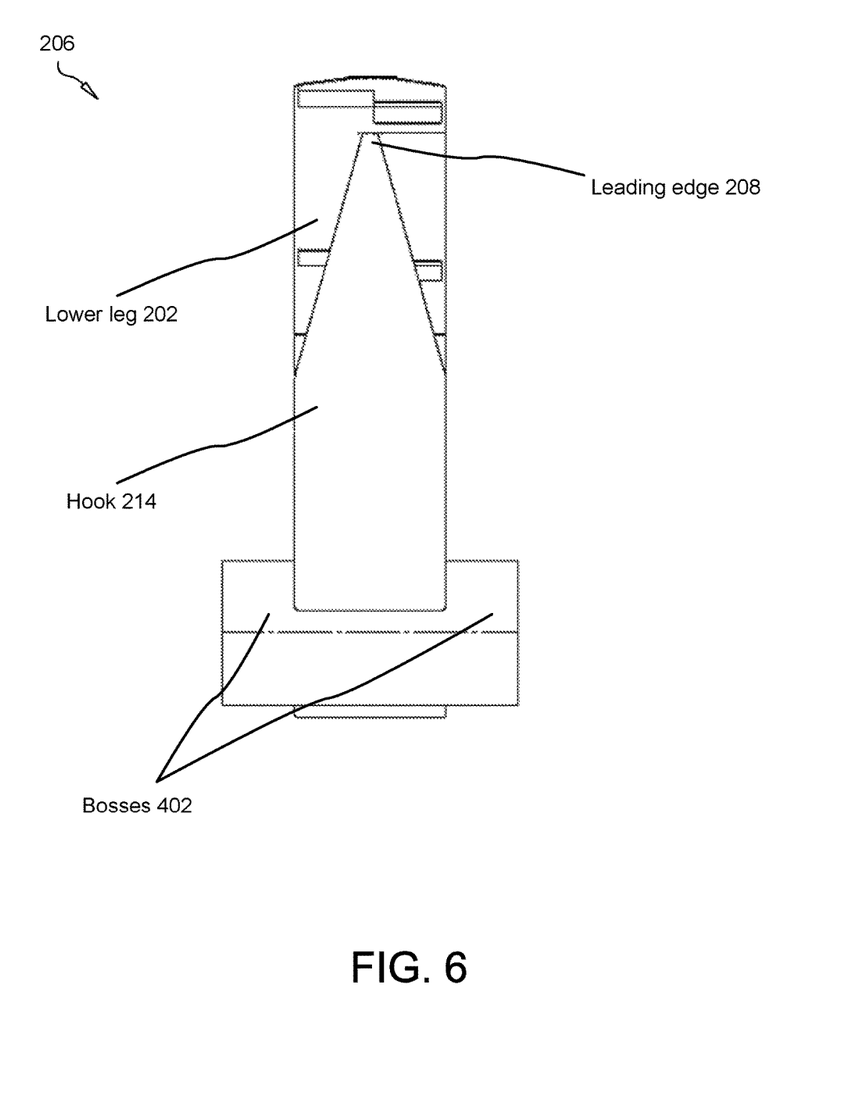
FIG. 6 is a top perspective view of the hook section of an improved surgical ligation clip in accordance with the present invention.

FIG. 6 is a top perspective view of the hook section of an improved surgical ligation clip 600 in accordance with the present invention.

The bosses 402 are shown, as is the hook 214 shown above the lower leg 202. Dimensions are shown, but actual dimensions may be greater or smaller than what is shown by a magnitude or ten or more.

Figure 7:
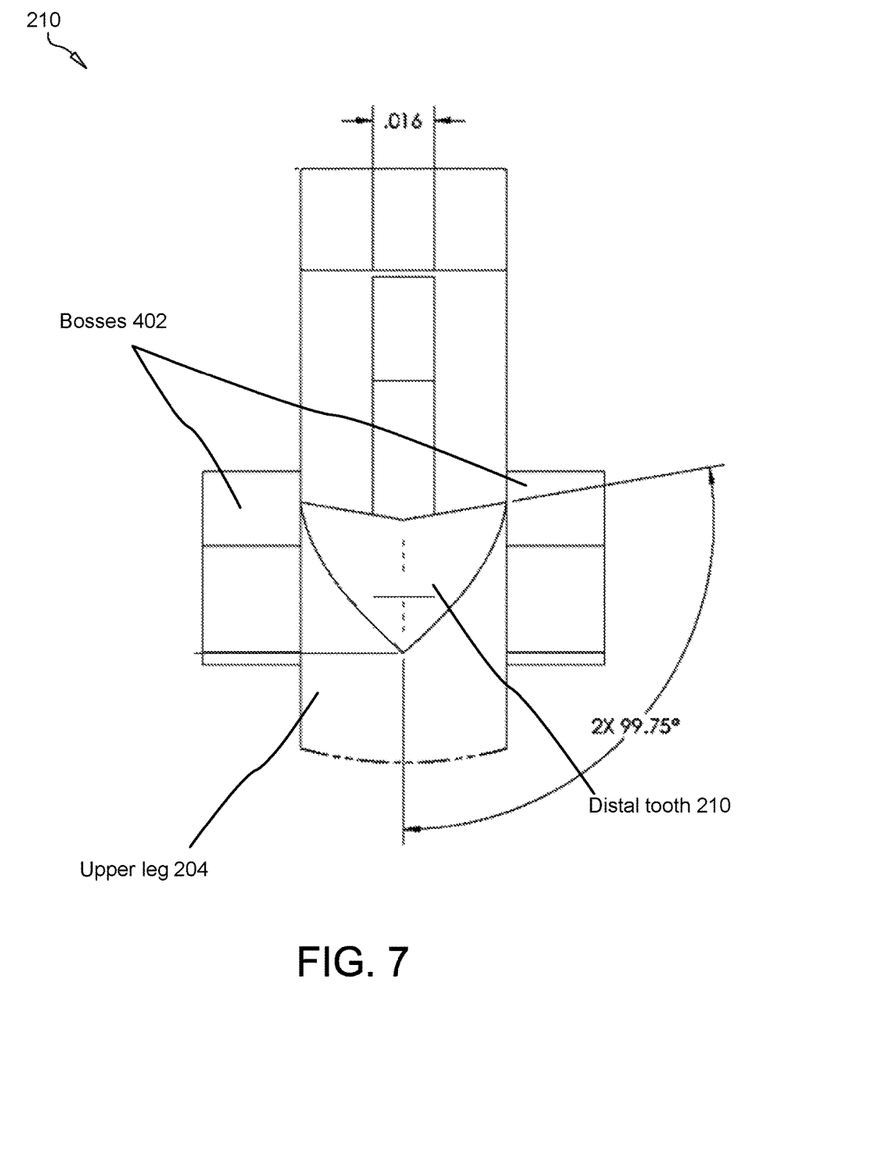
FIG. 7 is a top perspective view of the distal end of the upper leg of an improved surgical ligation clip in accordance with the present invention.

FIG. 7 is a top perspective view of the distal end of the upper leg of an improved surgical ligation clip in accordance with the present invention.

The bosses 402 are shown, as is the hook 214 shown above the lower leg 202. Dimensions are shown, but actual dimensions may be greater or smaller than what is shown by a magnitude or ten or more.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A polymeric surgical ligation clip, the surgical clip comprising:
    an elongated concave lower leg having a rearward end and a forward end;
    an elongated upper leg having a rearward end hingedly connected to the rearward end of the lower leg;
    a plurality of teeth protruding outwardly from one or more of the lower leg and the upper leg;
    a hook section jutting outwardly from the lower leg and cantilevers over the lower leg, the hook section and lower leg together defining a latching recess for engaging a distal end of the upper leg, the hook section having a forward edge and a rearward edge, the rearward edge sharpened for incising soft tissue when the surgical ligation clip is closed within soft tissue;
    an oblique flank connected to the distal end of the upper leg, the oblique flank extends from the upper leg at a location proximal to a terminal distal end of the upper leg; wherein the oblique flank protrudes outwardly from the upper leg to a point more distal than the terminal distal end of the upper leg; wherein a recess is created between a lower surface of the oblique flank and an upper surface of the upper leg, the oblique flank configured to clamp down over the leading edge to prevent damage to soft tissue during surgery and post-operatively.

2. The surgical clip of claim 1, wherein the oblique flank is formed as an integrated piece with the upper leg.

3. The surgical clip of claim 1, wherein the entire surgical clip is formed as one integrated piece.

4. The surgical clip of claim 1, wherein the distal end of the upper leg further comprises a distal tooth for piercing soft tissue.

5. The surgical clip of claim 1, further comprising a plurality of bosses for engaging jaws of an applier.

6. The surgical clip of claim 1, where a stress cavity is formed at the connection point of the upper leg and the lower leg.

7. The surgical clip of claim 1, wherein the hook further comprises a sharpened forward edge.

8. The surgical clip of claim 1, wherein the hook section further comprises a sharpened tip.

9. The surgical clip of claim 1, wherein the surgical clip is fabricated from one or more bioabsorbable materials.

10. The surgical clip of claim 1, wherein the surgical clip is rendered radio opaque.

11. A polymeric surgical ligation clip, the surgical clip comprising:
    an elongated concave lower leg having a rearward end and a forward end;
    an elongated upper leg having a rearward end hingedly connected to the rearward end of the lower leg;
    a plurality of teeth staggered protruding outwardly from one or more of the lower leg and the upper leg;
    a hook section jutting outwardly from the lower leg and cantilevers over the lower leg, the hook section and lower leg together defining a latching recess for engaging a distal end of the upper leg, the hook section having a sharpened tip for incising soft tissue when the surgical ligation clip is closed within soft tissue, the hook section having a sharpened leading edge and a sharpened rearward edge;
    an oblique flank connected to the distal end of the upper leg, the oblique flank extending from the upper leg at a location proximal to a terminal distal end of the upper leg; wherein the oblique flank protrudes outwardly from the upper leg to a point more distal than the terminal distal end of the upper leg; wherein a recess is created between a lower surface of the oblique flank and an upper surface of the upper leg, the oblique flank configured to clamp down over the hook section to prevent damage to soft tissue during surgery and post-operatively.

* * * * *